United States Patent [19]

Edwards et al.

[11] Patent Number: 4,649,205

[45] Date of Patent: Mar. 10, 1987

[54] PROCESS FOR THE MANUFACTURE OF MALEIC ANHYDRIDE UTILIZING CATALYSTS REACTIVATED WITH ALKYL ESTERS OF ORTHOPHOSPHORIC ACID IN THE PRESENCE OF WATER

[75] Inventors: Robert C. Edwards, Naperville; Carl A. Udovich, Joliet, both of Ill.

[73] Assignee: Standard Oil Company (Indiana), Chicago, Ill.

[21] Appl. No.: 706,034

[22] Filed: Feb. 27, 1985

Related U.S. Application Data

[63] Continuation-in-part of Ser. No. 484,949, Apr. 14, 1980, abandoned.

[51] Int. Cl.[4] .......................................... C07D 307/60
[52] U.S. Cl. ...................... 549/260; 502/38; 502/51; 549/257; 549/259
[58] Field of Search ............... 549/256, 257, 259, 260; 502/38, 51

[56] References Cited

U.S. PATENT DOCUMENTS 3,862,146  1/1975  Boghosian .......................... 549/260

FOREIGN PATENT DOCUMENTS 50-10714  4/1975  Japan .
1291354  10/1972  United Kingdom .
1464198  2/1977  United Kingdom .

Primary Examiner—Henry R. Jiles
Assistant Examiner—Bernard I. Dentz
Attorney, Agent, or Firm—Gunar J. Blumberg; William T. McClain; William H. Magidson

[57] ABSTRACT

A process for the reactivation of a vanadium-phosphorus-oxygen catalyst promoted by metals selected from the group consisting of zinc, molybdenum, niobium, tungsten, uranium, cobalt and tin with alkyl esters of phosphoric acid and water is disclosed. The catalysts are useful for the manufacture of maleic anhydride from butane, butene, butadiene or benzene feedstock.

12 Claims, No Drawings

PROCESS FOR THE MANUFACTURE OF MALEIC ANHYDRIDE UTILIZING CATALYSTS REACTIVATED WITH ALKYL ESTERS OF ORTHOPHOSPHORIC ACID IN THE PRESENCE OF WATER

RELATED APPLICATIONS

This is a continuation-in-part application of Ser. No. 484,949 filed Apr. 14, 1983, now abandoned.

FIELD OF THE INVENTION

The field of this invention relates to the activation or reactivation of phosphorus-vanadium co-metal-promoted catalysts with a hydrocarbon ester of phosphoric acid, in the presence of water wherein the amount of water added is about 1000 to about 40,000 parts per million of the reactor feed gas stream.

BACKGROUND

Maleic anhydride is of significant commercial interest throughout the world and is extensively used in the production of alkyd resins. It is also a versatile intermediate for chemical synthesis. Consequently, large quantities of maleic anhydride are produced each year to satisfy these needs.

In general, catalysts utilized for the oxidation of benzene and $C_4$ hydrocarbons, such as butene, butane, and butadiene, to maleic anhydride are based upon vanadium and phosphorus. Various metal activators have been used to enhance the phosphorus-vanadium catalyst. The difficulty with the phosphorus-vanadium metal-promoted catalysts is that they tend to deactivate quite quickly. In this connection, U.S. Pat. Nos. 4,020,174, 4,094,816, and 4,089,807 teach that carbon tetrachloride can be used to reactivate the vanadium-phosphorus co-metal-promoted catalyst. In U.S. Pat. No. 3,296,282 and U.S. Pat. No. 3,474,041, there is described a method for the regeneration of vanadium-phosphorus oxidation catalysts used in the oxidation of olefins to make maleic anhydride. These references disclose the process of treating the catalyst with a phosphine, phosphite or phosphonate by periodically or continuously passing the phosphorus compound to the reactor, with or without interrupting the olefin feed flow. British Patent Specification No. 1,464,198 teaches regeneration of phosphorus complexes with certain phosphates. This reference does not disclose the reactivation of vanadium-phosphorus co-metal catalysts in the presence of about 1000 to about 40,000 parts per million of water in the feed gas stream as capable of being regenerated by organic phosphates nor does it suggest that the phosphates used in regeneration improved the color stability of the resulting maleic anhydride. Particularly, the reference does not appreciate that water in excess of 100,000 to 500,000 parts per million by weight in the feed gas stream is deleterious to the catalyst reactivation process.

We have now discovered a method for regenerating in situ vanadium-phosphorus co-metal catalyst complexes used in the vapor-phase oxidation of benzene and $C_4$ hydrocarbons such as butane, butene and butadiene to maleic anhydride. According to our process, the vapor-phase oxidation of the $C_4$ hydrocarbons and benzene to maleic anhydride is conducted by contacting the hydrocarbon feedstock in the presence of a vanadium-phosphorus-oxygen catalyst promoted with metals selected from the group consisting of zinc, molybdenum, tungsten, niobium, cobalt, tin, manganese, nickel, and uranium. The preferred co-metals are molybdenum and zinc. The catalyst is regenerated continuously or by batch method as desired during the vapor-phase oxidation of $C_4$ hydrocarbons or benzene with an alkyl ester of orthophosphoric acid having the formula $(RO)_3P=O$, wherein R is hydrogen or a $C_1$ to $C_4$ alkyl, at least one R being a $C_1$ to $C_4$ alkyl. The preferred method is to regenerate the catalyst continuously because significantly better maleic anhydride yields are obtained.

The catalyst to be reactivated can be prepared in various ways including the one disclosed in U.S. Pat. No. 3,862,146, issued Jan. 21, 1975, having Edward M. Boghosian as its inventor. The catalyst can also be prepared according to the process disclosed in U.S. Pat. Nos. 4,418,003, 4,416,802 and 4,416,803. Alternatively, the catalyst to be reactivated can suitably be prepared from an alcohol solution which has been reacted with phosphorus pentoxide and has been saturated with an inorganic acid, such as hydrogen chloride. Other ways to prepare the catalyst are disclosed in U.S. Pat. No. 4,328,126 wherein the catalyst is made from an organic solvent system.

Precipitation of the phosphorus-vanadium co-metal mixed oxide can suitably be effected by azeotropic distillation of the organic solvent and the water of reaction and the subsequent evaporation of the organic solvent. The atomic ratio of vanadium to phosphorus can suitably be in the range of about 0.5:1 to about 1.25:1, preferably in the range of about 0.6:1 to about 1:1. The total atomic ratio of zinc or molybdenum or the other co-metals to vanadium is advantageously in the range of about 0.005:1 to about 0.25:1. The atomic ratio of phosphorus to vanadium is suitably in the range of about 2:1 to about 0.8:1, preferably about 1:1 to about 1.7:1. The reactivation of the catalyst can also suitably be conducted by dissolving the alkyl ester of phosphoric acid in water and applying this solution in a uniform manner to the catalyst to be regenerated. This method is particularly suitable in continuous processes which utilize multi-tubular upflow reactors. In this process, the alkyl ester, in an aqueous medium comprising about 0.001 to about 90 wt% of the alkyl ester is sprayed as a liquid into the feed gas stream flowing to the reactor. This process has great advantages over conventional additions of regenerating agents, which entail plant shutdowns, since, in our novel process, the reactivation is conducted in situ without interrupting production or utilizing a hot oil vaporizer which tends to decompose alkyl phosphates. Our continuous process for color stabilizing maleic anhydride obtained by the vapor-phase oxidation of benzene or $C_4$ hydrocarbons such as butane over a phosphorus-vanadium-oxygen catalyst promoted by a metal selected from the group consisting of zinc, molybdenum, niobium, tungsten, uranium, cobalt, and tin comprises regenerating the catalyst by contacting it during the vapor-phase oxidation with an alkyl ester of orthophosphoric acid having the formula $(RO)_3P=O$ where R is hydrogen or a $C_1$ to $C_4$ alkyl, at least one R being a $C_1$ to $C_4$ alkyl.

The continuous reactivation is applicable to phosphorus-vanadium catalysts and to phosphorus-vanadium catalysts promoted by metals, which are disclosed hereinabove. Suitable metals include molybdenum, zinc, tungsten, tin, cobalt, etc.

This invention also comprises a process for oxidizing benzene or $C_4$ hydrocarbons such as butane, butene, and butadiene to maleic anhydride by contacting it in the presence of oxygen with the continuously reactivated catalyst in the presence of about 1000 to about 40,000 parts per million by weight of water based on the total weight of the feed gas stream and for improving the color and color stability of maleic anhydride produced by our novel process employing continuous or batch catalyst regeneration. Generally the amount of alkyl ester added is about 0.1 to about 100,000 parts per million by weight of the reactor feed gas stream. In a preferred novel process using continuous catalyst regeneration, the amount of alkyl phosphate added is in the range of about 0.1 to about 30 parts per million by weight of the reactor feed stream. Higher concentrations of of alkyl phosphate generally above about 30 parts per million by weight are useful in a batch catalyst regeneration process, preferably in a range of about 50 to about 100,000 parts per million by weight of reactor feed gas stream and more preferably about 1000 to about 100,000 parts per million by weight of reactor feed gas stream. The reactivation is conducted at a temperature of about 650° to about 900° F. The alkyl phosphate in a water medium comprising about 0.001 to about 90 weight percent, more preferably about 0.01 to about 50 weight percent, of the solution is contacted with the feed gas stream flowing to the reactor. If desired, the water and alkyl phosphate may be added separately to the feed gas stream instead of as a solution. Alternatively, the alkyl phosphate and water may be added directly to the butane feed prior to the mixing of the butane and air reactants. The oxidation of butane to maleic anhydride may be accomplished by contacting n-butane in low concentration in oxygen with the described catalyst. Air is entirely satisfactory as a source of oxygen, but synthetic mixtures of oxygen and diluent gases such as nitrogen may also be employed. Air enriched with oxygen may be used.

The gaseous feed stream to the oxidation reactors will normally contain air and about 0.2 to about 1.7 mole percent of the hydrocarbon such as benzene, butane, butene or butadiene. About 0.8 to about 1.5 mole percent of the hydrocarbon is satisfactory for optimum yield of maleic anhydride for the process of this invention. Although higher concentrations may be employed, explosive hazards may be encountered. Lower concentrations of the hydrocarbon feedstock, less than about one percent, of course, will reduce the total yield obtained at equivalent flow rates and, thus, are not normally employed for economic reasons. The flow rate of the gaseous stream through the reactor may be varied within rather wide limits, but the preferred range of operations is at the rate of about 100 to about 4000 cc of feed per cc of catalyst per hour and more preferably about 1000 to about 2400 cc of feed per cc of catalyst per hour. Lower flow rates make the butane oxidation process uneconomical. A catalyst should be effective at flow rates of about 1200 to about 2400 cc of hydrocarbon feed per cc of catalyst per hour. There are catalysts which show good promise but when subjected to the hourly space velocity designated above show very poor yields. The amount of water added is about 1000 to about 40,000 parts per million by weight of the reactor feed gas stream. The preferred amount of water added is about 5000 to about 35,000 parts per million by weight of the reactor feed gas stream. Residence times of the gas stream will normally be less than about four seconds, more preferably less than about one second, and down to a rate where less efficient operations are obtained. The flow rates and residence times are calculated at standard conditions of 760 mm of mercury and at 0° C.

A variety of reactors will be found to be useful and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at a relatively constant temperature and some medium is needed to conduct heat from the reactors, such as lead and the like, but it has been found that eutectic salt baths are completely satisfactory. One such salt bath is a sodium nitrate, sodium nitrite, and potassium nitrate eutectic constant temperature mixture. An additional method of temperature control is to use a metal block reactor whereby the metals surrounding the tube act as a temperature regulating body. As will be recognized by one skilled in the art, the heat exchanger medium may be kept at the proper temperature by heat exchangers and the like. The reactor or reaction tubes may be iron, stainless steel, carbon steel, nickel, glass tubes such as vycor, and the like. Both carbon steel and nickel tubes have excellent long life under the conditions of the reaction described herein. Normally, the reactors contain a preheat zone containing an inert material such as one-quarter-inch Alundum pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other medium is to conduct heat away from the walls of the reactor and control the reaction. Better operations are normally obtained when the reaction temperature employed is no greater than about 20° to about 50° F. above the salt bath temperature. The temperature of the reactor, of course, will also depend to some extent upon the size of the reactor and hydrocarbon feedstock concentration.

The reaction may be conducted at atmospheric, superatmospheric or below atmospheric pressure. The exit pressure will be at least slightly higher than the ambient pressure to ensure a positive flow from the reactor. The pressure of the inert gases must be sufficiently higher to overcome the pressure drop through the reactor.

Maleic anhydride may be recovered by a number of ways well known to those skilled in the art. For example, the recovery may be by direct condensation or by absorption in suitable media, with specific operation and purification of the maleic anhydride. The following examples will serve to provide a fuller understanding of the invention, but it is to be understood that these examples are given for illustrative purposes only and should not be interpreted as limiting the invention in any way. In the examples, the terms "conversion", "selectivity" and "yield" are defined as follows:

$$\text{Conversion \%} = \frac{\text{Moles n-butane reacted}}{\text{Moles n-butane in feed}} \times 100$$

-continued $$\text{Selectivity \%} = \frac{\text{Moles maleic anhydride produced}}{\text{Moles n-butane feed consumed}} \times 100$$

$$\text{Yield Wt. \%} = (\text{Conversion}) \times (\text{Selectivity}) \times 169$$

EXAMPLE 1

A phosphorus-vanadium catalyst promoted with zinc gave a yield of 87 wt.% at 792° F., 2000 volume hourly space velocity (VHSV), and 1.5% n-butane in a 0.62 inch internal diameter pilot reactor having a 33 inch catalyst bed. The feed contained 10,000 ppm of water at this time. After 524 additional hours on stream, at the above conditions, and at 780° F., the catalyst gave an 80 wt% yield of maleic anhydride. Triethylphosphate, 1.4 ppm, was added to the feed gas stream 48 hours later along with the 10,000 ppm of water. After another 192 hours, the yield had improved to 85 wt.% at 799° F. and the same conditions. The water was removed from the feed stream 521 hours later while continuing with 1.4 ppm of triethylphosphate addition. After another 160 hours, the yield declined to 73 wt.% at 779° F. and the same flow conditions. Upon increasing the triethylphosphate addition to 3.2 ppm 194 hours later, the yield declined further; 336 hours after this, the yield was only 55 wt.% at 780° F. and the same flow conditions. Water was reintroduced after 24 hours at 10,000 ppm and the alkylphosphate addition was discontinued. After 120 hours, the yield had improved to 77 wt.%. This example illustrates that a combination of water and alkylphosphate ester is necessary for the optimum regeneration of catalysts. Note that without water addition the alkylphosphate addition actually resulted in a yield decline with this particular catalyst.

As shown in Example 1, the use of water with alkylphosphate esters is very important. Prolonged addition of alkylphosphate without the co-addition of water can result in a yield decline. This decline is dependent on the catalyst used. The use of water and alkylphosphate esters gives better results when compared to the use of alkylphosphates without water.

EXAMPLE 2

A 6 cc load of a vanadium-phosphorus-zinc catalyst, having an atomic ratio of 1/1.2/0.18 in the form of 3/16-inch cylindrical tablets, was used to oxidize n-butane to maleic anhydride in a 0.62 inch internal diameter minireactor. A 1.05% n-butane in air mixture was passed through the catalyst at greater than 1700 VHSV at a temperature between 750°–790° F. Under these conditions after 1056 hours of continuous reaction, the yield of maleic anhydride was 84 wt.% at 77% butane conversion and 65% selectivity. Under the same conditions after 3048 hours of operation, the yield of maleic anhydride was 75 wt.% at 80% butane conversion and 55% selectivity. After 3384 hours of operation, 0.16 cc of a 1:1 by volume mixture of trimethylphosphate in water was passed through the reactor by means of injection into the feed gas stream over a 20-second period. The yield of maleic anhydride after 4008 hours of operation was 82.4 wt.% at 77% conversion and 64% selectivity.

EXAMPLE 3

A load in excess of 1000 g of a vanadium-phosphorus-molybdenum catalyst, having an atomic ratio of 1/1.3/0.03 in the form of 3/16 inch cylindrical tablets, was used to oxidize butane to maleic anhydride in a large pilot reactor. A 1.5% n-butane in air mixture was passed through the catalyst at up to 2000 VHSV at a temperature of between 720°–769° F. Under these conditions after 1050 hours, the yield of maleic anhydride was 86 wt.% at 84% conversion and 61% selectivity. After 1863 hours of operation, the yield of maleic anhydride was 81 wt.% at 84% conversion and 57% selectivity. After 1870 hours of operation, an aqueous solution containing 5.1 g of triethylphosphate per liter of water was placed in the feed gas stream before the reactor. The feed stream was passed through this solution so as to saturate the feed under selected conditions. After an additional twenty-four hours, the saturator solution was reduced to 0.5 g of triethylphosphate per liter of water and for the remaining time on stream, the reaction was operated under these conditions. After 2400 hours of continuous operation, the yield of maleic anhydride was 86 wt.% at 80% conversion and 64% selectivity.

EXAMPLE 4

Triethylphosphate was continuously added to the feed gas stream of a maleic anhydride reactor by passing a heated, pressurized inert gas stream through a heated vessel containing triethylphosphate and injecting this saturated inert gas stream into the feed gas. The addition rate of the triethylphosphate was controlled by varying the temperature and/or the flow rate of the inert gas. The yield of maleic anhydride was increased from 80 wt.% to 92 wt.% and the selectivity was increased from 61 mole% to 70 mole% at 1200 VHSV and 1.4 mole% n-butane feed using this procedure to continuously apply $4 \times 10^{-3}$ g triethylphosphate per kg of catalyst per hour.

EXAMPLE 5

Triethylphosphate, 0.053 g per g of catalyst, was continuously added to the feed gas of a maleic anhydride reactor by pumping it through a steam-jacketed line and spraying it into the feed gas. Using this procedure, the yield of maleic anhydride increased from 71 wt.% to 75 wt.% after nine days at 1600 VHSV and 1.4 mole% n-butane feed.

EXAMPLE 6

Using the procedures described in Example 4, triethylphosphate was added to a maleic anhydride catalyst. Before triethylphosphate addition, the maleic anhydride quality as measured by aged molten color averaged 65 APHA over a one-month time period ranging from 25–300 APHA. After triethylphosphate was added, the aged molten color averaged 35 APHA with a range of 20–60 APHA. Also, fractionator purges required to remove by-products and color bodies from the crude maleic anhydride decreased from 4.7% to 1.9% of the net maleic anhydride produced.

EXAMPLE 7

A phosphorus-vanadium-molybdenum catalyst prepared according to the method reported in U.S. Pat. No. 4,418,003 was removed from a large pilot plant. Samples, 6 cc, of this catalyst in the form of 3/16 inch cylindrical pellets were loaded into three 0.62 inch internal diameter minireactors. For each minireactor, a 1.08 mole% n-butane in air mixture was passed through a water saturator and then over the catalyst at 1500 VHSV and 750°–810° F.

After 145 days on stream, the catalysts in the three reactors gave approximately the same yields (70–73 wt.%) as shown in Table I. On day 147, a solution of 50% water and 50% triethylphosphate was added to the saturator of reactor B and 100% triethylphosphate was added to the saturator of reactor C. After 153 days on stream, there was no change in reactor A which still had 100% water in the saturator, the yield from reactor B increased by 6 wt.%, and the yield from reactor C decreased by 3 wt.%. On day 156, the yield from reactor B reached 83 wt.% which is a 13 wt.% increase in yield from adding triethylphosphate and water to the feed gas stream. At day 165, the yield of reactor A changed only slightly to 74 wt.%. Significantly, reactor C after 167 days on stream also showed only a 1 wt.% increase in yield although triethylphosphate was being added to the feed gas stream for 20 days. During this time period, about 10 g of triethylphosphate were added to the feed stream of reactor C. For this phosphorus-vanadium-molybdenum catalyst, the addition of triethylphosphate without water produced no significant increase in yield.

TABLE I

| Reactor | Days on Stream | Feed Saturator Composition | Temp., °F. | Conv., Mole % | Yield, Wt. % |
|---|---|---|---|---|---|
| A | 145 | 100% Water | 752 | 86 | 73 |
|   | 147 | 100% Water | 752 | — | — |
|   | 153 | 100% Water | 746 | 86 | 73 |
|   | 165 | 100% Water | 741 | 84 | 74 |
| B | 145 | 100% Water | 765 | 86 | 70 |
|   | 147 | 50% Water 50% Triethylphosphate | 765 | — | — |
|   | 153 | 50% Water 50% Triethylphosphate | 767 | 78 | 76 |
|   | 156 | 50% Water 50% Triethylphosphate | 798 | 77 | 83 |
| C | 145 | 100% Water | 771 | 86 | 72 |
|   | 147 | 100% Triethylphosphate | 771 | — | — |
|   | 153 | 100% Triethylphosphate | 776 | 86 | 69 |
|   | 167 | 100% Triethylphosphate | 752 | 84 | 73 |

EXAMPLE 8

A phosphorus-vanadium-zinc catalyst prepared according to the method of U.S. Pat. No. 3,862,146 was removed from a commercial reactor. A sample of this catalyst, 166 g, in the form of 3/16 inch cylindrical pellets, was charged to a tubular pilot plant reactor having an internal diameter of 0.62 inch. This reactor was operated at 2000 VHSV of 1.5 mole% n-butane in air. An Isco metering pump was used to accurately add water and triethylphosphate to the reactor feed gas stream. After the reactor bed was lined out at the above conditions, the metering pump was used to add a constant 10 ppm of triethylphosphate to the feed gas stream while varying the water concentration from 1000–40,000 ppm.

The results of this experiment are summarized in Table II. With 10,000 ppm of water in the feed and no triethylphosphate, the yield was 57 wt.% after 456 hours on stream. After this, 10 ppm of triethylphosphate were added to the feed along with the 10,000 ppm of water. The yield at 1320 hours on stream was 75 wt.% at a salt bath temperature of 819° F. At this time, the water concentration was reduced to 5000 ppm while the triethylphosphate concentration was kept at 10 ppm. The yield declined to 72 wt.% at 1464 hours. Increasing the water concentration to 15,000 ppm caused the yield to increase to 76 wt.% at 1968 hours. Reducing the water concentration to 1,000 ppm gave a yield of only 70 wt.% after 2448 hours. A significant increase in water concentration to 40,000 ppm increased the yield to 73 wt.%; however, this is 3 wt.% below the level reported for 15,000 ppm. Thus, the optimum water concentration is somewhere between 10,000 and 40,000 ppm.

TABLE II

| Hours on Stream | Feed Water Conc., ppm | Feed Triethylphosphate Conc., ppm | Salt Temp., °F. | Conv., Mole % | Yield, Wt. % |
|---|---|---|---|---|---|
| 456 | 10,000 | 0 | 772 | 81 | 57 |
| 457 | 10,000 | 10 | 772 | — | — |
| 1320 | 10,000 | 10 | 819 | 80 | 75 |
| 1321 | 5,000 | 10 | 819 | — | — |
| 1464 | 5,000 | 10 | 801 | 81 | 72 |
| 1585 | 15,000 | 10 | 817 | — | — |
| 1968 | 15,000 | 10 | 821 | 81 | 76 |
| 1969 | 1,000 | 10 | 821 | — | — |
| 2448 | 1,000 | 10 | 829 | 80 | 70 |
| 2449 | 40,000 | 10 | 829 | — | — |
| 2736 | 40,000 | 10 | 815 | 83 | 73 |

EXAMPLE 9

Using the same catalyst bed and reactor from Example 8, the feed was changed to 1.4 mole% n-butane in a 1:1 mixture of air and steam. The triethylphosphate concentration in the feed was maintained at 10 ppm. Before changing the feed composition the maleic anhydride yield was 73 wt.% with 85% conversion at 2000 VHSV of 1.5 mole% n-butane and a salt bath temperature of 809° F. When the feed composition change was made, the maleic anhydride yield rapidly dropped within 6 hours to 67 wt.% with 79% conversion at 2000 VHSV and a salt bath temperature of 860° F. This example shows that operating with 50 wt.% water in the reactor feed gas stream causes a rapid decline in catalyst performance.

EXAMPLE 10

A phosphorus-vanadium-oxygen catalyst promoted by zinc was loaded into a large tubular reactor having a reactor tube internal diameter of 0.88 inch and a catalyst bed length of 165 inches. This reactor was cooled by a circulating salt bath. A feed stream of 1.0–1.6 percent n-butane in air was passed over this catalyst bed at 730°–850° F. to produce maleic anhydride. After the catalyst was fully activated, a maximum maleic anhydride yield of 88 wt.% was achieved after 90 days on stream at a hydrocarbon throughput of 1.745 lbs of hydrocarbon (96% n-butane) per lb of catalyst per day and a salt bath temperature of 772° F. The productivity was 1.47 lbs maleic anhydride per lb of catalyst per day. As shown in Table III, decreasing the throughput gives an increase in the maleic anhydride yield, but a significant reduction in productivity occurs.

The yield of this catalyst began to decline with further time on stream until at 167 days the yield was only 81 wt.% with a hydrocarbon throughput of 1.021 lbs hydrocarbon per lb of catalyst per day. At this time, triethylphosphate addition to the reactor feed stream was started. At 199 days, the yield improved to 90 wt.% at a throughput of 1.495 lbs hydrocarbon per lb of catalyst per day (Table III).

By adjusting the triethylphosphate and water addition rates, the yield of the catalyst did not decline when hydrocarbon throughput was increased from 1.767 to 1.994 lbs hydrocarbon per lb of catalyst per day. As shown in Table III, an increase in throughput gave a decrease in yield prior to the start of this treatment. Thus, a significant increase in productivity to 1.76 lbs maleic anhydride per lb of catalyst per day was achieved.

TABLE III

Reactor Performance and Productivity

| Days on Stream | lb Hydrocarbon/ lb Catalyst-Day | Salt Bath Temp., °F. |
|---|---|---|
| 90 | 1.745 | 772 |
| 105 | 0.952 | 754 |
| 106 | 1.495 | 770 |
| 167 | 1.021 | 741 |
| 167 | STARTED Triethylphosphate Addition | |
| 199 | 1.495 | 772 |
| 650 | 1.767 | 795 |
| 657 | 1.903 | 794 |
| 696 | 1.994 | 802 |

| lb Triethylphosphate/ lb Catalyst-Day | Feed H$_2$O Conc., ppm | Conv., Mole % |
|---|---|---|
| | | 78 |
| | | 78 |
| | | 80 |
| | | 77 |
| 0.79 × 10$^{-4}$ | 1.0 × 10$^4$ | 79 |
| 1.51 × 10$^{-4}$ | 1.0 × 10$^4$ | 84 |
| 1.46 × 10$^{-4}$ | 1.0 × 10$^4$ | 84 |
| 2.17 × 10$^{-4}$ | 1.2 × 10$^4$ | 85 |

| Yield on n-Butane, Wt. % | lb Maleic Anhydride/ lb Catalyst-Day |
|---|---|
| 88 | 1.47 |
| 92 | 0.84 |
| 91 | 1.31 |
| 81 | 0.79 |
| 90 | 1.29 |
| 92 | 1.56 |
| 92 | 1.68 |
| 92 | 1.76 |

We claim:

1. A continuous process for the vapor-phase oxidation of butane feedstock to form maleic anhydride in which butane is contacted in the presence of molecular oxygen or air at an hourly space velocity about 1000 to 4000 cubic centimeters of feed per cubic centimeter of catalyst per hour with a vanadium-phosphorus-oxygen catalyst promoted by zinc or molybdenum wherein the catalyst is regenerated continuously by contacting it during the vapor-phase oxidation with water and an alkyl ester of orthophosphoric acid having the formula $(RO)_3P=O$ where R is hydrogen or a $C_1$ to $C_4$ alkyl, at least one R being a $C_1$ to $C_4$ alkyl, wherein the amount of water added is about 1000 parts per million to about 40,000 parts per million by weight of the reactor feed gas stream and the amount of the alkyl ester added is about 0.1 parts per million to about 100,000 parts per million by weight of the reactor feed gas stream.

2. The process of claim 1 wherein the alkyl ester is triethylphosphate.

3. The process of claim 1 wherein the alkyl ester is trimethylphosphate.

4. The process of claim 1 wherein the reaction temperature is about 650° F. to about 900° F.

5. The process of claim 1 wherein a fixed-bed catalyst is used and the feedstock contains about 0.2 to about 1.7 mole percent butane and the hourly space velocity is in the range of about 1000 to about 2400 cubic centimeters of feed per cubic centimeter of catalyst per hour.

6. A continuous process for the reactivation of a vanadium-phosphorus-oxygen co-metal catalyst promoted with one or more co-metals selected from the group consisting of zinc, molybdenum, niobium, tungsten, uranium, cobalt and tin which process comprises applying to the catalyst during the vapor phase oxidation of butane to maleic anhydride water and an alkyl orthophosphoric acid having the formula $(RO)_3P=O$ where R is hydrogen or a $C_1$ to $C_4$ alkyl, at least one R being a $C_1$ to $C_4$ alkyl, wherein the amount of water added is about 5000 parts per million to about 35,000 parts per million by weight of the feed gas stream.

7. The process of claim 6 wherein the alkyl ester is triethylphosphate and the amount of the alkyl ester added is about 0.1 parts per million to about 100,000 parts per million by weight of the reactor feed gas stream.

8. The process of claim 6 wherein the alkyl ester is trimethylphosphate and the amount of the alkyl ester added is about 0.1 parts per million to about 100,000 parts per million by weight of the reactor feed gas stream.

9. A continuous process for the reactivation of a vanadium-phosphorus-oxygen co-metal catalyst promoted with co-metals selected from the group consisting of zinc and molybdenum which process comprises applying to the catalyst during the vapor phase oxidation of butane to maleic anhydride water and an alkyl ester of orthophosphoric acid having the formula $(RO)_3P=O$ where R is hydrogen or a $C_1$ to $C_4$ alkyl, at least one R being a $C_1$ to $C_4$ alkyl, wherein the amount of water added is about 1000 parts per million to about 40,000 parts per million by weight of the feed gas stream and the amount of the alkyl ester added is about 0.1 parts per million to about 100,000 parts per million by weight of the reactor feed gas stream.

10. The process of claim 9 wherein the alkyl ester is either triethylphosphate or trimethylphosphate.

11. The process of claim 9 which process comprises applying continuously about $2 \times 10^{-4}$ to about 0.2 gram of an alkyl ester of orthophosphoric acid having the formula $(RO)_3P=O$ where R is hydrogen or a $C_1$ to $C_4$ alkyl, at least one R being a $C_1$ to $C_4$ alkyl, per kilogram of the catalyst per hour and water, wherein the amount of water added is about $1 \times 10^{-3}$ to about 0.1 kilogram per hour per kilogram of catalyst.

12. A continuous process for the reactivation of a vanadium-phosphorus-oxygen co-metal catalyst promoted with one or more co-metals selected from the group consisting of zinc, molybdenum, niobium, tungsten, uranium, cobalt and tin which process comprises applying to the catalyst during the vapor phase oxidation of butane to maleic anhydride water and an alkyl ester of orthophosphoric acid having the formula $(RO)_3P=O$ where R is hydrogen or a $C_1$ to $C_4$ alkyl, at least one R being a $C_1$ to $C_4$ alkyl, wherein the amount of water added is about 1000 parts per million by weight to about 40,000 parts per million of the feed gas stream.

* * * * *